(12) United States Patent
Clynch

(10) Patent No.: US 6,463,351 B1
(45) Date of Patent: Oct. 8, 2002

(54) METHOD FOR PRODUCING CUSTOM FITTED MEDICAL DEVICES

(75) Inventor: George S. Clynch, Calgary (CA)

(73) Assignee: Clynch Technologies, Inc., Calgary (CA)

( * ) Notice: Subject to any disclaimer, the term of this patent is extended or adjusted under 35 U.S.C. 154(b) by 0 days.

(21) Appl. No.: 09/341,413
(22) PCT Filed: Jan. 8, 1997
(86) PCT No.: PCT/CA97/00009

§ 371 (c)(1),
(2), (4) Date: Oct. 14, 1999

(87) PCT Pub. No.: WO98/30176

PCT Pub. Date: Jul. 16, 1998

(51) Int. Cl.[7] .............................. A61F 2/50; G06F 19/00
(52) U.S. Cl. ....................... 700/163; 700/182; 700/197; 623/901
(58) Field of Search ........................... 700/163, 97, 98, 700/117, 118, 182, 183, 197; 623/27, 33, 901; 264/40.1; 702/153

(56) References Cited

U.S. PATENT DOCUMENTS

| 5,228,164 A | 7/1993 | Graf et al. ................. 12/133 R |
| 5,252,822 A | 10/1993 | Firth ..................... 250/227.11 |
| 5,270,795 A | 12/1993 | Blais ......................... 356/375 |
| 5,432,703 A | 7/1995 | Clynch et al. .......... 364/474.05 |
| 5,911,126 A | * 6/1999 | Massen ..................... 702/153 |

FOREIGN PATENT DOCUMENTS

| DE | 4232606 | 3/1994 |
| DE | 4417872 | 11/1995 |
| EP | 0574098 | 12/1993 |
| EP | 0555207 | 10/1995 |
| GB | 2188846 | 10/1987 |
| NL | 8902888 | 6/1991 |
| WO | WO94 18638 | 8/1994 |

* cited by examiner

Primary Examiner—Leo P. Picard
Assistant Examiner—Steven R. Garland
(74) Attorney, Agent, or Firm—Price, Heneveld, Cooper, DeWitt & Litton (57) ABSTRACT

A method for producing a medical device, such as a prosthetic or orthotic structure which makes the procedure more widely available at less cost. The method involves making a model of the body part for which a medical structure is to be manufactured using conformable fabric impregnated with a settable resin. The model may be prepared by a physician or a prosthetist who has no direct access to an expensive digitizing scanner. The model is removed from the patient's body part and shipped to a scanning facility where a digitizing scanner is used to produce a digitized image of the model. The digitized image is shrunk to compensate for the thickness of the model and the digitized data file is preferably sent back to the physician or prosthetist who manipulates the digitized image using a customized software program to produce a modified data file. The modified data file is sent to the scanning facility where the modified data file is converted into control code for a machine which produces a mold used in the manufacture of the medical device. The mold may be manufactured at the scanning facility or the modified data file may be uploaded to the manufacturing facility which may manufacture the mold as well as the medical device. The method is also adapted for use in producing many other medical or anthropometric devices which requires a precision fit to the human body.

20 Claims, 3 Drawing Sheets

FIG. 3

METHOD FOR PRODUCING CUSTOM FITTED MEDICAL DEVICES

TECHNICAL FIELD

This invention relates to a methods of producing medical devices such as prosthetic and orthotic structures and, in particular, to a method of manufacturing such devices in a manner that makes the devices more widely available to the public at less cost.

BACKGROUND OF THE INVENTION

The manufacture of medical devices such as prosthetic and orthotic structures is well known in the art and described for example in European Patent No. EP 0 555 207 which issued to Clynch Technologies Inc. on Oct. 11, 1995, and its United States counterpart, U.S. Pat. No. 5,432,703 which issued to the same patentee on Jul. 11, 1995. These patents describe a system and a method for producing a medical device such as a prosthetic or orthotic structure having a surface for engagement with a portion of the human body. The system produces a more accurately fitting socket and involves a less time-consuming process with less discomfort to the patient than other prior art methods. The socket is made from a mold that is produced from a three dimensional image of the portion of the body requiring the medical device. The three dimensional image is obtained by scanning the body surface requiring the device, the body surface being supported within a reflective, stretchable stocking on which non-reflective markings are placed to indicate sensitive areas of the body surface as well as insensitive areas capable of bearing a load. The scanned image therefore includes void-points coincident with the non-reflective markings on the stocking surface. The digitized image is manipulated to produce a modified digital image by selectively adjusting certain discreet modification sites to produce areas of enlargement and adjusting other discreet modification sites to produce areas of reduction. A mold is produced from the modified data by converting the data into control code for controlling the operation of a machine for producing the mold using the image data. An orthotic structure is manufactured using the mold whereby the areas of enlargement correspond to non-load bearing modification sites and the areas of reduction correspond to load bearing modification sites so that sensitive areas of the body part are relieved of pressure and load bearing areas of the body part are positioned at the areas of reduction to facilitate load bearing. This method has proven to be very effective in producing custom fitted prosthetic and orthotic devices which are comfortable to wear and provide extended service.

In spite of the recognized advantages of this method, laser digitizing equipment is expensive. Public access to the benefits of the invention is therefore curtailed.

It is therefore a primary object of the present invention to provide a method of producing medical devices such as prosthetic and orthotic devices which reduces the cost of production and makes the benefits of the technology more widely available to the general public.

It is a further object of the invention to provide a method for producing a medical device such as a prosthetic or orthotic structure more economically without sacrificing the optimal custom fit that may be obtained using a digitized three dimensional image that is modified at selected sites to provide maximum comfort.

SUMMARY OF THE INVENTION

These and other objects of the invention are achieved by a method for producing a structure for use in a prosthetic, orthotic or other medical device having a surface for engagement with a portion of the human body, including the steps of defining the body portion and presenting an outer surface thereof for laser digitizing, inspecting the body portion and identifying critical areas on the outer surface with small non-reflective markings, scanning the body portion with a laser digitizer to produce a plurality of closely spaced longitudinal lines read by the laser digitizer, storing the contour coordinates representing a digital image as data including void-points produced by the non-reflective markings, displaying the digital image graphically and identifying basic modification areas for said inner surfaces of said structure by way of the location of the void-points, identifying selected vertices within the basic modification areas, producing modified data by moving the selected vertices for some of the basic modification areas in a positive direction relative to non-selected surrounding vertices to produce build-ups and moving selected vertices of other basic modification areas in a negative direction relative to non-selected surrounding vertices to produce areas of reduction, using said modified data to produce control code for controlling a machine for producing a mold having a surface contoured in the likeness of the body surface, but including areas of build-up and areas of reduction, and producing the structure from the mold whereby the areas of build-up provide areas of relief in the surface of the structure and the areas of reduction provide higher pressure areas in the surface of the structure, the improvement comprising:

covering the surface of the body portion with a conformable reflective material that can be activated to make a model of the body portion;

inspecting the body portion and identifying critical areas on the material with non-reflective markings;

activating the material to harden and produce the model of the body portion;

removimg the model from the body portion and scanning the model to produce a digitized image of the model;

shrinking the digitized image to accurately represent the body portion by compensating for the thickness of the model; and manipulating the compensated digitized image to provide areas of build-up and relief in the medical device, whereby the manipulated compensated digitized image is used to produce code for controlling a machine for producing a mold or an anthropometric device having a surface contoured in the likeness of the body portion, but including the areas of build-up and relief.

The method in accordance with the invention therefore provides a mechanism for decentralizing most of the process of producing medical devices such as prosthetic or orthotic structures as well as other anthropometric devices. The decentralization is enabled by the use of a conformable reflective material which can be used to make a substantially rigid model of the body portion requiring the medical or anthropometric device. Such a model can be made in a physician's office or clinic without the use of expensive equipment. The model is produced by covering the surface of the body portion with the conformable reflective material that can be activated to form a hardened structure. Preferably, the conformable reflective material is impregnated with a plastics resin which is activated by the application of water. In accordance with the procedure, the body portion is covered with the conformable reflective material and critical areas of the covered body portion are identified on the material covering with non-reflective markings. The non-reflective markings are preferably applied before the material is activated to harden and produce a model of the body portion. This permits the physician or prosthetist to palpate the bony areas of the body portion to determine the exact location of critical areas before the material is hardened to form the model. After the critical areas are indicated by the non-reflective markings, the material is activated to harden or produce the model. Once the model has hardened, it is removed from the body portion and shipped to a scanning facility which scans the model to produce a three dimensional image, for example, in the manner described above in the European and United States patents to Clynch Technologies Inc. The three dimensional image is thereafter preferably downloaded to a computer system of the physician which produced the model. The physician's computer system is equipped with a custom computer aided design (CAD) software application which permits the image to be manipulated and modified with the assistance of a database of default modifications for each modification site indicated by the non-reflective markings. After the digitized image is modified to provide a custom fit most suited for the body part, the image is uploaded by the physician to the scanning center where it is converted into control code for controlling a machine for producing a mold, such as a milling machine for example. The control code is then uploaded to the machine for producing the mold and a mold is produced using the control code. In certain instances, a mold is not produced. Instead, an anthropometric device is produced directly by the machine using the control code. This is the case when a device such as a custom arch support, a custom seat or the like is produced from the scanned image of the model. The milling machine may be located at the scanning facility or, alternatively, at a device manufacturing facility which produces the medical or anthropometric device. Regardless of where it is located, the device manufacturing facility uses the mold and related specifications to produce the medical or anthropometric device, which is shipped to the physician's office for any final fitting and/or adjustments that may be required.

In the method in accordance with the invention, a scanning facility preferably serves a plurality of physician's clinics which communicate with the scanning facility via a telecommunications service such as the Internet or by a couriered medium such as diskette or CD Recordable. Furthermore, a plurality of scanning facilities may be served by a single device manufacturing facility which may also communicate with the scanning facilities by a telecommunications service such as the Internet or a hard storage medium exchanged by courier or the like. The invention thus permits a much wider distribution of the technology because it obviates the requirement for expensive image digitizing equipment at every service provider's clinic and permits patients to be treated by local physicians who have access to the technology at minimal cost.

BRIEF DESCRIPTION OF THE DRAWINGS

The invention will now be further explained by way of example only and with reference to the following drawings, wherein.

DETAILED DESCRIPTION OF THE PREFERRED EMBODIMENTS

Figure 1:
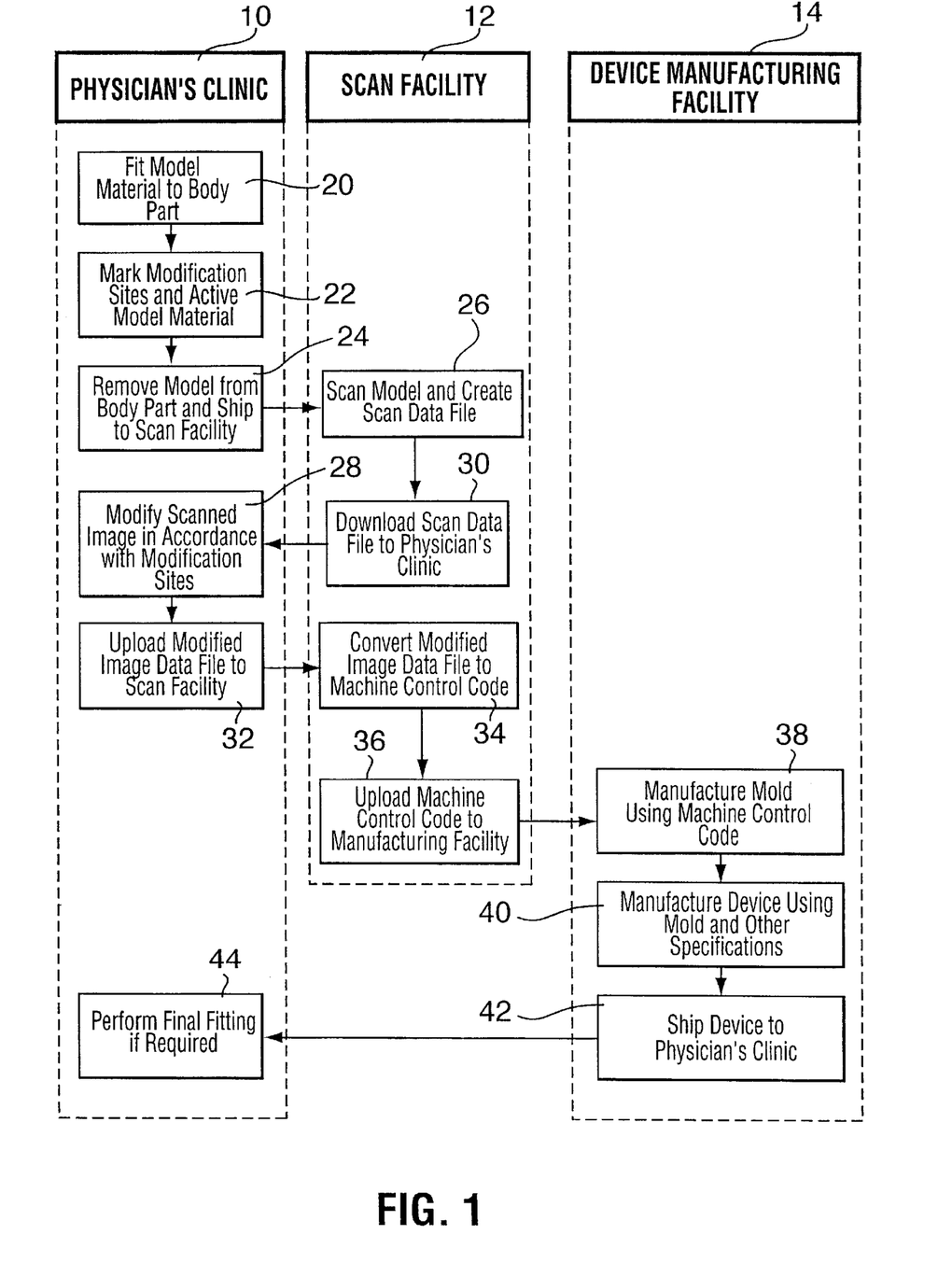
FIG. 1 is a block diagram illustrating the production of medical devices using a method in accordance with the invention.

FIG. 1 is a block diagram illustrating the production of medical or anthropometric devices using a method in accordance with the invention. FIG. 1 is organized to show a general flow of the steps of the method as well as one preferred organization of the entities for accomplishing the method. The method is preferably practiced by professionals such as physicians who offer medical services to the public, scan facilities which serve a plurality of physicians, and device manufacturing facilities which may produce medical or anthropometric devices for a number of scan facilities.

The physicians may be prosthetists, orthopedic surgeons, podiatrists, radiologists or plastic surgeons and other professionals may be industrial designers of custom protective gear, sports gear, or equipment for handicapped individuals. Each of these professionals at least periodically require or can benefit from the practice of the method in accordance with the invention. The prosthetists practice the invention to provide prosthetic devices such as artificial limbs. Orthopedic surgeons, orthotists, and podiatrists may practice the invention to provide orthotic devices such as braces and/or supports for weak or ineffective joints or muscles, including compression garmets to correct skeletal disorders such as scaliosis. Radiologists may practice the invention to provide locators and/or stabilizers for positioning patients requiring radiotherapy to ensure that patients are immobilized during a radiotherapy treatment and to ensure that radiation is accurately focused on the target tissue. Plastic surgeons may use the invention for designing implants and/or tracking and documenting the effects of plastic surgery. The industrial designers may practice the invention for any anthropometric application, including the production of precision fit coverings to support or protect the human anatomy, such as custom seats for wheelchairs, etc. and protective or performance enhancing gear for sport or occupational activities including clothing, footwear, helmets or body armor and the like.

For the sake of simplicity, the description of the preferred embodiment that follows refers exclusively to "medical devices," but the description equally applies to any anthropometric device, i.e any article adapted for precision fit to the human body. Likewise, the description refers to "physician", but the description applies equally to any professional involved in the precision fitting of devices to the human body, and "clinic" means any place where such fitting occurs.

The scan facility 12 is equipped with equipment for capturing a three dimensional optical image of a target surface, in converting the image into a digitized data file which provides data that may be displayed and manipulated on a computer workstation. The currently preferred technology for the scanner is described in U.S. Pat. No. 5,270,795 which issued Dec. 14, 1993 to The National Research Council of Canada. U.S. Pat. No. 5,270,795 describes an imaging system that is a modification of the Biris imaging system in that it employs an apertured mask, while at the same time employing some aspects of the triangulation imaging system, and in addition employing a validation of the image spots detected in the camera. In other words, the camera has the ability to distinguish between false spots generated by clutter and those spots that truly represent a reflected point on the target surface. Use of the scanner will be discussed in more detail below with reference to FIG. 2.

The device manufacturing facility 14 manufactures the medical devices and may serve a plurality of scan facilities.

Figure 3:
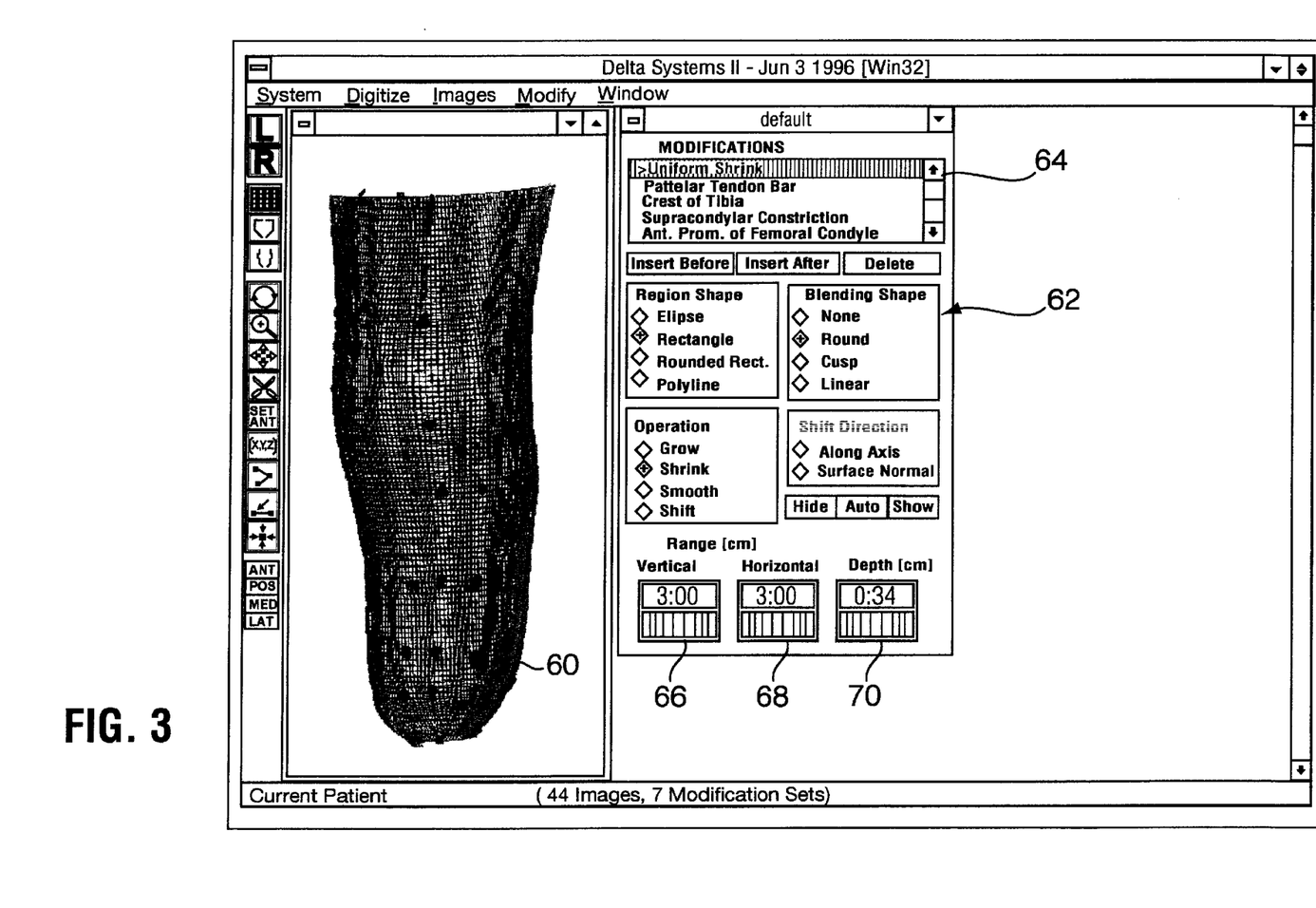
FIG. 3 shows an example of the software in accordance with the invention for manipulating three dimensional images of body portions require medical devices.

In accordance with the method, the process of constructing a medical device begins in a physician's clinic 10 where in a step 20, a modelling material is fitted to the body part of a patient requiring a medical device. As described above, the medical device may be a prosthetic, orthotic, radiological or any other anthropometric precision fit device. The modelling material is preferably a conformable, reflective, stretchable material impregnated with a curable substance which hardens on curing. In this specification, conformable means a material which assumes the shape and contour of an article over which it is draped or around which it is wrapped. The word reflective means light in colour and capable of reflecting light, either laser light or white light, but it does not necessarily mean shiny or iridescent or otherwise more reflective of light than any surface that is light in colour. A suitable modelling material is described in U.S. Pat. No. 5,228,164 which issued on Jul. 20, 1993 to Graf et al. The material described in that patent is a knitted fabric having sufficient extensibility and memory to be applied to a body part and conform to the shape of the body part. The fabric is impregnated with a curable resin which is preferably a water curable, isocyanate-functional prepolymer. This modelling material may be purchased in tubular or sheet form and once cured provides a substantially rigid three dimensional model of the body part to which it is applied, the model having a certain amount of memory so that it will regain its original cured shape after limited deformation. As a general rule, after the modelling material is fitted to the body part in step 20, the body part is inspected and modification sites are marked with non-reflective markings in a manner described in the applicant's issued European Patent No. 0 555 207. The modification sites are preferably marked prior to activation of the modelling material to harden it so that the physician can properly palpate the body part to accurately ascertain the location for each modification site. In certain instances, for example, when a prosthetic structure for a limb such as a leg is being produced, it is desirable to use a tubular modelling material that is suspended in a manner that permits the patient to load the material with a certain body weight during the modification site marking process. Once the modification sites have been marked, the modelling material is activated to harden it. In accordance with the currently preferred modelling material, activation is accomplished by the application of water which initiates a curing process that hardens the material after a few minutes. When the modelling material is sufficiently hardened to retain its shape, the hardened model is removed from the body part in step 24 and packed for shipment to the scan facility 12. In some instances, removal may involve cutting or partially cutting the model from the body part. On receipt of the model at the scan facility 12, it is supported in a proper orientation for scanning, preferably using a laser scanner. The scanning process in step 26 creates a scan data file which must be converted to an image data file as will be described in more detail below. Preferably, the image data file is downloaded to the physician's clinic in a step 28 to permit the physician, who is most familiar with the requirements for the medical device, to modify the scanned image in accordance with the marked modification sites in step 30. It is possible for the scan facility 12 to modify the scanned image if the physician does not have the software necessary to manipulate the scanned image. After the scanned image is modified, as will be described in more detail in relation to FIG. 1, the modified scan image file is uploaded to the scan facility where a special software program is used in step 34 to convert the modified image file to machine control code, a G-code for example. The machine control code is used to control a machine such as a milling machine for producing a mold which is a replica of the modified three dimensional image created in step 30 or an anthropometric device which is a negative rendering of the modified three dimensional image. The control code is then uploaded to the manufacturing facility 14 where it is used to manufacture the mold using the machine control code in step 38. Alternatively, the machine for manufacturing the mold may be located at the scan facility in which case the mold or the device is manufactured at the scan facility. In the case of a mold, it is then shipped to the device manufacturing facility along with related specifications for producing the medical device. The related specifications include such information as the type of device, and in the case of a limb, the dimensions and appendages required, etc. After the mold is produced in step 38, the device is manufactured using the mold and related specifications in step 40. In step 42, the manufactured device is shipped to the physician's clinic where any final fitting and/or adjustments are accomplished in step 44. As used hereinafter in this document, the word "mold" means either a positive or a negative reproduction of the modified scanned image from a suitable stock material. A positive reproduction is one in which the mold has an outer surface that is a reproduction of the modified three-dimensional image. Conversely, the machine control code may be transposed so that an anthropometric device is machined directly from a suitable stock, in a negative type reproduction of the modified three-dimensional image.

As can be readily appreciated, this method permits physicians to provide optimal prosthetic, orthotic or anthropometric devices at minimal cost. The only investment required by the physician is the software for modifying scanned images. Otherwise, equipment commonly available in the physician's office may be used to practice the procedure.

Figure 2:
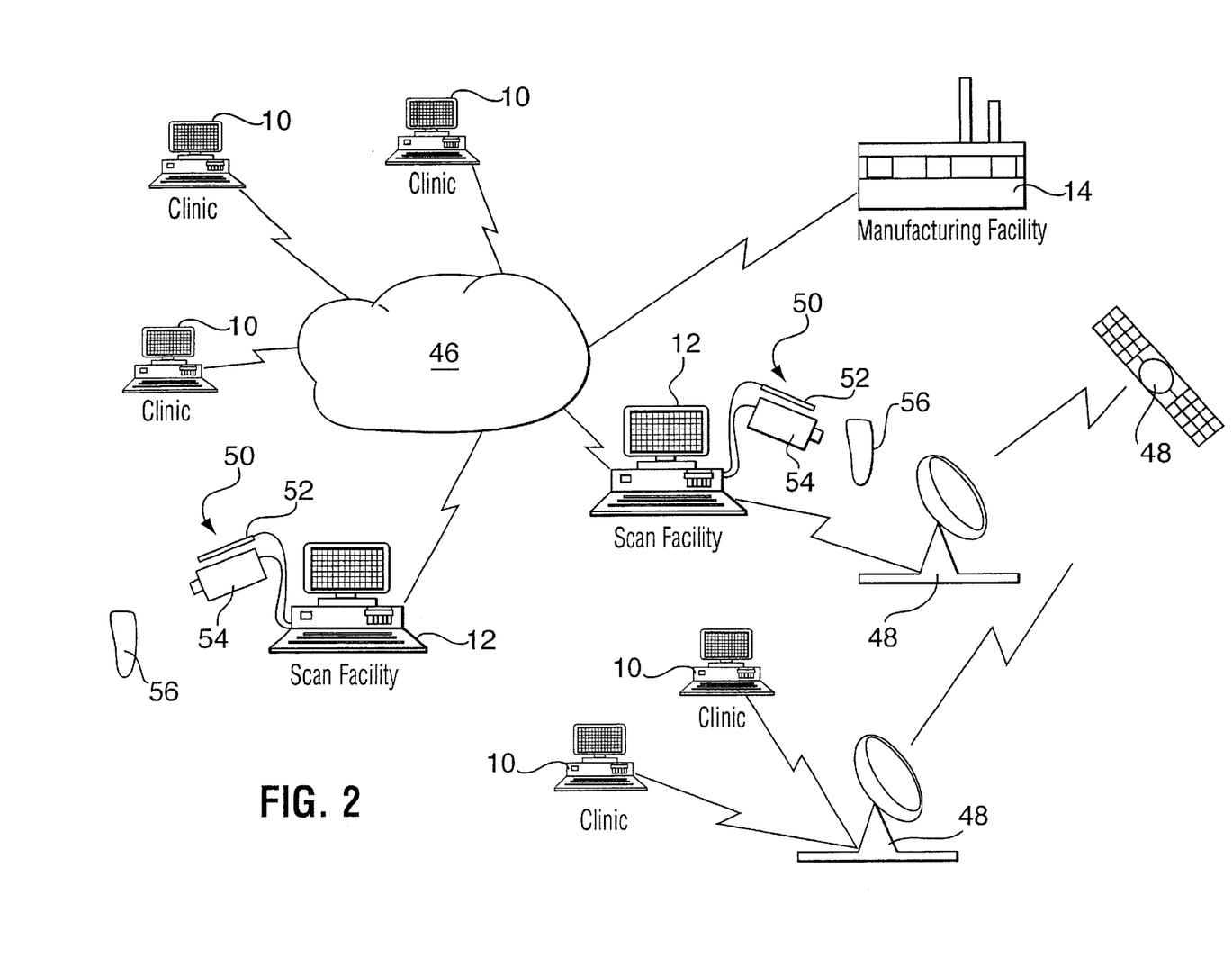
FIG. 2 is a schematic diagram illustrating the interrelationship of entities in a decentralized method of production in accordance with the invention.

FIG. 2 shows the preferred arrangement of facilities for manufacturing medical devices using the method in accordance with the invention. A plurality of clinics 10 are served by one or more scan facilities 12 which are in turn served by one or more manufacturing facilities 14. The clinics 10 preferably communicate with the scan facilities using a telecommunications service such as the Internet, graphically illustrated and indicated by reference 46. In many remote locations such as the Canadian north, the only communication available may be by satellite and remote clinics may be connected with scan facilities using satellite communication equipment 48, which is well known in the art and commercially available. Each scan facility 12 is equipped with at least one high precision 3-D laser scanner system generally indicated by reference 50. Each scanner system includes an illumination source 52, which is preferably an optical laser, and an optical camera 54 used to detect lumination reflected from a model 56 of a body part for which a medical device is to be created. The model 56 is supported in a predetermined relationship and orientation with respect to the high precision 3-D laser scanner 50 which is operated in a known manner to scan the model 56. If the scanner system 50 is an imaging system as described in U.S. Pat. No. 5,270,795, about four to six scan images are required to scan a cylindrical object such as a model of a residual limb. In a current implementation, four 3-D laser scanners 50 are mounted to a circular ring (not illustrated), each scanner being aimed at a center of the ring. The entire ring is adapted to move vertically under computer control. This configuration permits imaging of any model of the human body. Identical scan data can also be obtained by rotating the model or the scanner by 90 degrees after each vertical scanner acquisition. The acquired images must be amalgamated into a complex three dimensional object. That amalgamation may be accomplished using several known methods. An acceptable method is respectively described in "A Volumetric Method for Building Complex Models from Range Images" (Computer Graphics Proceedings, Annual Conference Series, 1996; Brian Curless and Mark Levoy, Stanford University, Pages 303–312) and "Marching Triangles: Range Image Fusion for Complex Object Modelling" (International Conference on Imaging Processing, 1996; A. Hilton, A. J. Stoddart, J. Illingworth and T. Windeatt; Department of Electronic and Electrical Engineering, University of Surrey, Guildford, U.K.).

FIG. 3 shows a screen print of the currently preferred implementation of the CAD application for modifying the scanned image of a model of a body part for which a medical device is to be produced. This implementation of the software application is written in the C++ language and may be executed by any personal computer system equipped with a 32-bit Windows (Windows is a trademark of Microsoft Corporation, Redmond, Wash. U.S.A.) compatible operating system, commonly available in most physician's clinics. The digitized scanned image 60 of the model is displayed in a window on the left hand side of the monitor. The modeled image shown is that of a below knee amputation, but any body portion may be imaged, including a foot, knee, leg, hip, back, shoulder, torso, arm, hand, neck or head for example. A pull down menu 62 is displayed in a window adjacent the scanned image. The pull down menu 62 includes the default options for modifying the scanned image to produce a mold to be used in the manufacture of the medical device or to produce a medical device directly from the modified image. The list of default modifications is available on a scrolling sub-menu 64. The options on the scrolling sub-menu depend on the type of medical device to be produced. Regardless of the type of device, a "uniform shrink" and a "smooth" option are available to permit the image to be uniformly shrunk in order to compensate for the thickness of the model and yield an accurately dimensioned image representative of the body part for which the device is to be produced. The smooth option converts the surface of the modified image into a smooth surface having the appearance of the mold that will be produced from the machine code generated from the modified image. Other options on the modification menu, as noted above, are device dependent. For example, the options available for a below knee prosthetic device include modifications for: Patellar Tenon Bar, Crest of Tibia, Supracondylar Constriction, Anterior Prominence of Femoral Condyle, Anterior Latter Tibial Prominence, Head of the Fibula Lateral Femoral Condyle, Distal End of the Fibula, Adductor Tubercal, Distal End Extension, and Posterior Wall Extension.

The default modification set for a knee orthosis includes Crest of Tibia, Anterior Lateral Tibial Prominence, Supracondylar Constriction, Medial Anatomical Joint and Lateral Anatomical Joint.

The default modification set for a podiatric orthosis include modifications directed to correcting/relieving the effects of plantar fasiitis or calcaneous heel spur, Metatarsalgia or Morton's Neuroma, sesamoiditis and pescavus.

Each of these default modifications are stored in a database of imperically derived data based on prior successful medical devices. When a default modification is selected, the shape and location of the modification is displayed on the image and updated on the pull down modification menu 62. Factors such as the regional shape, blending shape, operation and shift direction may be controlled using radio buttons. The vertical and horizontal blending range are also controllable using virtual dial wheels 66, 68 and the depth of the modification can be adjusted using a virtual dial wheel 70 in order to ensure that the modification conforms to the requirements of the patient. In addition, the size and shape of the modification can be manipulated using the computer's mouse by dragging coloured symbols indicating the borders of the region within which the modification will take place, the application area and the horizontal and vertical blending ranges surrounding the modification site.

Further detail concerning the manipulation of such images is available in European Patent No. 0 555 207, as noted above. The methodology employed for podiatric devices is similar to the method used for fabrication of knee orthoses and below knee prosthetics. As in the procedures described above, a stretch stockinet or nylon may be pulled over the application area, in this case the foot, to prevent the modelling fabric from adhering to hair, etc. A modelling fabric is then pulled over top of the nylon/stocking, thus encapsulating the treatment area. The marking sequence for this application (as in all other applications) may be undertaken prior to or following the fitting of the modelling material. The markings may be applied directly to the foot, to the stocking, or to the modelling fabric. The non-reflective markings indicate areas that require modification either for correction or for preventative measures. All modifications are intended as a template for the fabrication of a device which provides optimal support to the human foot. The following is the marking procedure for designing a custom foot orthosis or custom footwear. If the diagnosis is plantar fasiitis or calcaneous heel spur the prominency of the calcaneous heel spur is marked, as is the medial longitudinal arch, the lateral arch, and the transverse arch. If the diagnosis is Metatarsalgia or Morton's Neuroma, the apex of the five metatarsal heads are marked. If the diagnosis is sesamoiditis, the first metatarsal is marked. Before activating the catalyst impregnated in the modelling material, it is important that the foot is held in a good biomechanical position. To do this it can be in either a fully loaded position, partially loaded, or non-loaded. For feet with pescavus, it is imperative that the foot be held in a good biomechanical position before activating the modelling material to harden it. Once the modelling material is activated, the material will harden. The hardened model is then removed. The result is a model which precisely represents all contours and features of the patient's foot. As in other applications, this model is imaged using a laser camera, and a positive mold of the foot or an orthotic device can be milled using a Computer Numerically-Controlled (CNC) milling machine. If a positive mold is the object produced it can be used as a last for the fabrication of footwear.

Other modification data sets are also under development for the medical and anthropometric devices discussed above. Although specific modification sites may vary depending on the application, the principles of device configuration remain the same.

INDUSTRIAL APPLICABILITY

The present invention provides a method for producing medical devices such as prosthetic, orthotic and precision fit devices useful in improving the quality of life of individuals who have suffered an amputation of a limb or an acquired or congenital defect which renders joints or muscles ineffective. It also provides a method for producing other medical and non-medical devices which require a precision fit to the human body. There is a significant demand for such services. A disadvantage of the known methods for producing medical devices of this type is the significant investment in equipment required to capture a digitized representation of the affected body part and convert the digitized representation into a digitized image which can be manipulated to form a modified image useful in producing machine code to control a machine for forming a mold that may be used to manufacture the medical device. The present invention provides a method for decentralizing most of the process of producing medical devices so that the majority of the work involved in the process of obtaining a modified digital image of the affected body part can be accomplished in a local physician's clinic to which the patient has ready access. This makes the service much more universally available to a wider spectrum of the population and reduces the cost of production because expensive equipment can be concentrated in specialized facilities. The method in accordance with the invention therefore places the best technology at the disposal of more practitioners and permits improvement in the quality of life of a larger number of individuals.

It will be apparent to those skilled in the art that the apparatus and the steps of the method described above may be alternately distributed. For example, the scan facility may be operated by one or more physicians who also treat patients and produce medical devices for those patients. Alternatively, the scan facility and the manufacturing facility may be one and the same. Likewise, it is possible for the physician who makes the initial mold of the patient's body part to provide adequate information for the scan facility to modify the digitized image directly without further input from the physician. This makes the procedure even more widely available since the physician need only be supplied with modelling material and adequate training to permit the physician to use the modelling material and provide the additional information necessary to modify the scanned image file at the scan facility. Other combinations and permutations may also be envisioned by those skilled in the art.

In view of these potential permutations of the method in accordance with the invention, it is intended that the scope of the invention be limited solely by the scope of the appended claims.

I claim:

1. A method for producing a structure for use in a prosthetic, orthotic or other medical device having a surface for engagement with a portion of the human body, including the steps of defining the body portion and presenting an outer surface thereof for laser digitizing, inspecting the body portion and identifying critical areas on the outer surface with small non-reflective markings, scanning the body portion with a laser digitizer to produce a plurality of closely spaced longitudinal lines read by the laser digitizer, storing contour coordinates representing a digital image as data including void-points produced by the non-reflective markings, displaying the digital image graphically and identifying basic modification areas for inner surfaces of said structure by way of the location of the void-points, identifying selected vertices within the basic modification areas, producing modified data by moving the selected vertices for some of the basic modification areas in a positive direction relative to non-selected surrounding vertices to produce build-ups and moving selected vertices of other basic modification areas in a negative direction relative to non-selected surrounding vertices to produce areas of reduction, using said modified data to produce control code for controlling a machine for producing a mold having a surface contoured in the likeness of the body surface, but including areas of build-up and areas of reduction, and producing the structure from the mold whereby the areas of build-up provide areas of relief in the surface of the structure and the areas of reduction provide higher pressure areas in the surface of the structure, the method further comprising:

covering the surface of the body portion with a comfortable reflective material that can be activated to harden and make a model of the body portion;

inspecting the body portion and identifying critical areas with non-reflective markings on the material;

activating the material to harden and produce the model of the body portion;

removing the model from the body portion and scanning the model to produce a digitized image of the model;

shrinking the digitized image to accurately represent the body portion by compensating for the thickness of the model; and manipulating the compensated digitized image to provide areas of build-up and relief in the medical device, whereby the manipulated, compensated digitized image is used to produce code for controlling a machine for producing a mold or an anthropometric device having a surface contoured in the likeness of the body portion, but including the areas of build-up and relief.

2. The method as claimed in claim 1 wherein the material that can be activated to harden and make a model of the body portion is a knitted fabric impregnated with a curable plastics resin.

3. The method as claimed in claim 2 wherein the curable plastics resin is activated by the application of water to the material.

4. The method as claimed in claim 1 wherein the model is shipped to a facility for scanning where the model is scanned and the compensated digitized image is produced.

5. The method as claimed in claim 4 wherein the model is produced by a physician having access to a computerized system for manipulating the compensated digitized image and the compensated digitized image data is provided by the scanning facility to the physician who manipulates the compensated image to produce the modified data.

6. The method as claimed in claim 4 wherein the facility for scanning the model is a facility that serves a plurality of physicians and/or prosthetists.

7. The method as claimed in claim 6 wherein the compensated digitized image is electronically downloaded to the physicians' computerized system.

8. The method as claimed in claim 7 wherein the compensated digitized image is electronically downloaded using a telecommunications service.

9. The method as claimed in claim 8 wherein the telecommunications service is the Internet.

10. The method as claimed in claim 1 wherein the scanner includes an imaging device having a position detector with an apertured mask in a converging lens system and the digitized image is a three dimensional reconstruction of multiple range images.

11. The method as claimed in claim 1 wherein the machine for producing a mold is operated by a medical device manufacturing facility that is remote from a scanning facility.

12. The method as claimed in claim 11 wherein the manufacturing facility serves a plurality of scanning facilities.

13. The method as claimed in claim 11 wherein the code for controlling a machine for producing a mold or an anthropometric device having a surface contoured in the likeness of the body portion is electronically uploaded from the scanning facility to the manufacturing facility.

14. The method as claimed in claim 13 wherein the code for controlling a machine is uploaded using a telecommunications service.

15. The method as claimed in claim 1 wherein the machine for producing a mold having a surface contoured in the likeness of the body portion is located in a scan facility and the mold is shipped to the manufacturing facility which manufactures the medical device using the mold and related specifications.

16. The method as claimed in claim 1 wherein the medical device is an artificial limb.

17. The method as claimed in claim 1 wherein the medical device is a support or brace for weak or ineffective joints or muscles.

18. The method as claimed in claim 1 wherein the medical device is a device for positioning a patient for radiotherapy or laser surgery.

19. The method as claimed in claim 1 wherein the medical device is used for protecting a part of the human body.

20. An anthropometric device produced using the method of claim 1.

* * * * *

UNITED STATES PATENT AND TRADEMARK OFFICE
CERTIFICATE OF CORRECTION

PATENT NO.    : 6,463,351 B1                                              Page 1 of 1
DATED         : October 8, 2002
INVENTOR(S)   : George S. Clynch It is certified that error appears in the above-identified patent and that said Letters Patent is hereby corrected as shown below:

Column 1,
Line 5, "methods" should be -- method --.

Column 3,
Line 67, "require" should be -- requiring --.

Column 5,
Line 64, "FIG. 1" should be -- FIG. 3 --.

Signed and Sealed this

Fourth Day of March, 2003

JAMES E. ROGAN
*Director of the United States Patent and Trademark Office*